(12) United States Patent
Ye et al.

(10) Patent No.: US 7,474,919 B2
(45) Date of Patent: Jan. 6, 2009

(54) LASER-BASED METHOD AND SYSTEM FOR ENHANCING OPTICAL BREAKDOWN

(75) Inventors: Jing Yong Ye, Ann Abor, MI (US);
Theodore B. Norris, Dexter, MI (US);
James R. Baker, Jr., Ann Arbor, MI (US); Lajos P. Balogh, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 739 days.

(21) Appl. No.: 10/637,343

(22) Filed: Aug. 8, 2003

(65) Prior Publication Data
US 2004/0043081 A1 Mar. 4, 2004

Related U.S. Application Data

(60) Provisional application No. 60/407,018, filed on Aug. 29, 2002, provisional application No. 60/406,861, filed on Aug. 29, 2002.

(51) Int. Cl.
*A61N 1/30* (2006.01)
(52) U.S. Cl. .................. 604/20; 606/2; 606/3; 606/6; 606/10; 604/22
(58) Field of Classification Search ............. 604/20–23; 424/280.1; 606/2–10; 128/24
See application file for complete search history.

(56) References Cited

U.S. PATENT DOCUMENTS 6,146,375 A * 11/2000 Juhasz et al. ................ 606/6

| | | | |
|---|---|---|---|
| RE37,585 E | 3/2002 | Mourou et al. | |
| 6,391,020 B1 * | 5/2002 | Kurtz et al. | 606/2 |
| 6,471,968 B1 * | 10/2002 | Baker et al. | 424/280.1 |

FOREIGN PATENT DOCUMENTS

WO    WO 01/87348    11/2001

OTHER PUBLICATIONS

Jing Yong Ye et al. "Enhancement of laser-induced optical brakdown using metal/dendrimer nanocomposites" Applied Physics Letters, Mar. 11, 2002, AIP, USA, vol. 80, No. 10.*
Ye, Jing Yong, et al., Enhancement of Laser-Induced Optical Breakdown Using Metal/Dendrimer Nanocomposites, Applied Physics Letters, vol. 80, No, 10, Mar. 11, 2002.

* cited by examiner

*Primary Examiner*—Kevin C Sirmons
*Assistant Examiner*—Phillip Gray
(74) *Attorney, Agent, or Firm*—Brooks Kushman P.C.

(57) ABSTRACT

An additive, preferably in the form of metal nanoparticles or nanodomains, greatly improves a laser-based method and system for inducing optical breakdown. The use of ultrashort laser pulses to induce laser-induced breakdown (LIB) in metal nanoparticles or nanocomposites makes it possible to reduce significantly the threshold laser energy required for LIB. Such nanoscale (submicron) metallic particles allows one to control the LIB process. The nanoparticles can be synthesized so as to target specific biological structures or tissues (dendrimer nanoparticles are one system for which this has been demonstrated). This opens up the possibility of performing LIB for targeted cancer treatment or microsurgery.

52 Claims, 3 Drawing Sheets

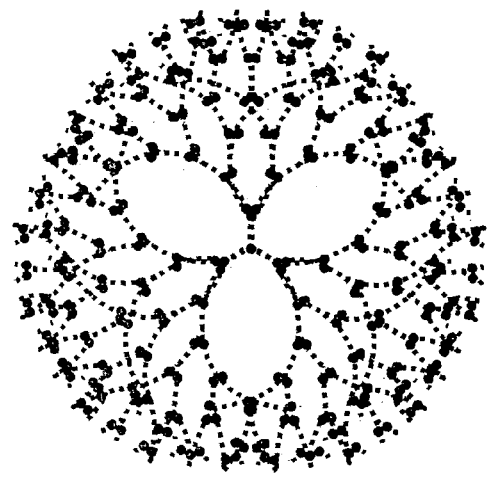
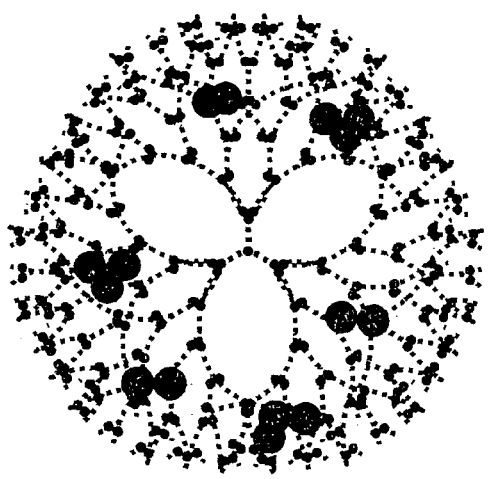
Fig. 1a    Fig. 1b
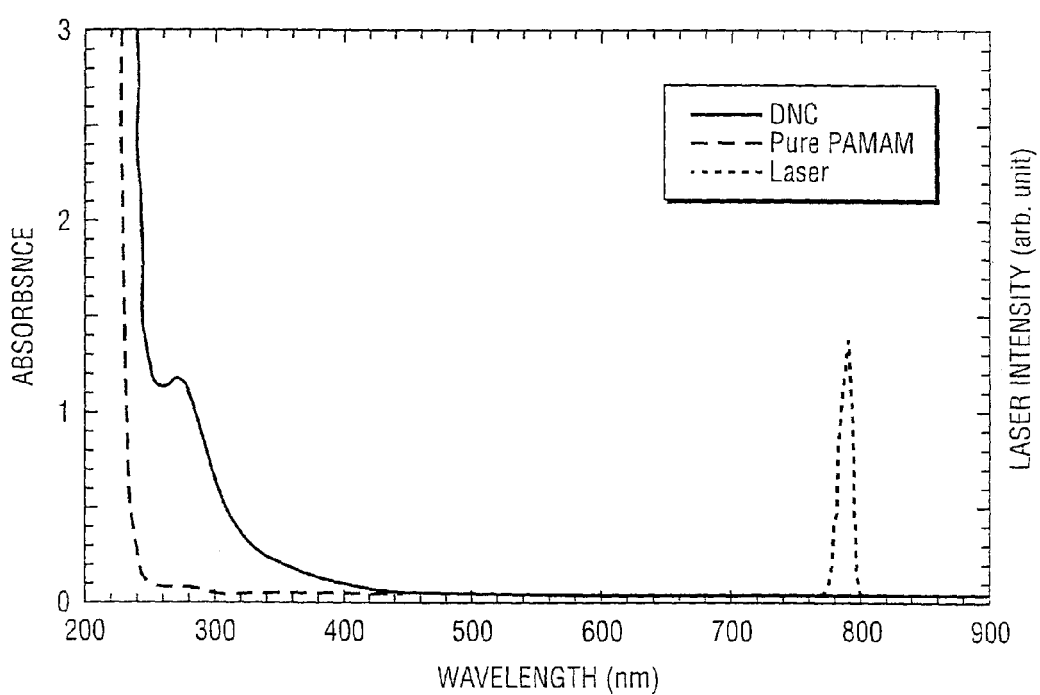
Fig. 1c

LASER-BASED METHOD AND SYSTEM FOR ENHANCING OPTICAL BREAKDOWN

CROSS-REFERENCE TO RELATED APPLICATIONS

This application claims the benefit of U.S. provisional application Ser. No. 60/407,018, filed Aug. 29, 2002, and Ser. No. 60/406,861, also filed on Aug. 29, 2002.

STATEMENT REGARDING FEDERALLY SPONSORED RESEARCH OR DEVELOPMENT

This invention was made with Government support under Contract No. NOI-CO-97111 from the National Cancer Institute, National Institute of Health. The Government has certain rights in the invention.

BACKGROUND OF THE INVENTION

1. Field of the Invention

This invention relates to laser-based methods and systems for enhancing optical breakdown.

2. Background Art

Much effort has been devoted to research on laser-induced optical breakdown (LIOB) since the advent of powerful lasers, because of the importance of LIOB in diverse fields including laser surgery, micromachining, three-dimensional optical data storage, solid state physics, etc. For example, U.S. Pat. No. 6,146,375 discloses a device for internal surface sclerostomy and U.S. Pat. No. 6,391,020 discloses a system for destroying material using optical radiation and ultrasound waves.

Recently, in order to obtain an in-depth understanding of the mechanism for LIOB and to find a controllable way for carrying out LIOB, extensive experimental and theoretical investigations have been focused on the laser parameter dependence of the breakdown threshold of optical materials and biological tissues. For example, U.S. Pat. No. RE 37,585 discloses a method to localize laser-induced breakdown.

The breakdown threshold, on the other hand, is also determined by the nature of the material itself. So far, much less attention has been paid to altering the breakdown threshold and achieving a controllable breakdown by modifying the material, although LIOB in well-designed materials has a wide range of potential applications.

Dendrimers are a class of macromolecules possessing a highly-branched three-dimensional architecture and well-controlled size, shape and functionality. U.S. Pat. No. 6,471,968 discloses a multifunctional nanodevice platform in the form of dendrimer complex.

SUMMARY OF THE INVENTION

An object of the present invention is to provide an improved laser-based method and system for enhancing optical breakdown by altering the LIOB threshold of a composition or material by incorporating an additive such as metal nanoparticles into the composition which significantly enhances the electric field localized at their immediate surroundings.

In carrying out the above object and other objects of the present invention, a laser-based method for enhancing optical breakdown is provided. The method includes providing a composition having an additive incorporated therein. The composition has a desired photodisruption threshold substantially lower than a photodisruption threshold of the composition without the additive. The method also includes generating at least one laser pulse having a predetermined pulse characteristic based on the desired photodisruption threshold. The method further includes propagating the at least one laser pulse through the composition to a photodisruption region determined by the location of the additive in the composition. The additive decreases the photodisruption threshold associated with the at least one laser pulse in the vicinity of the additive.

The composition may include at least one nanodevice having the additive and a linked agent targeted to a specific biological structure or tissue.

The at least one nanodevice may include a dendrimer-based nanodevice.

The additive may include metal nano particles or domains.

The composition may include polymer macromolecules which are a host for the additive.

The polymer macromolecules may form at least one dendrimer-based nanodevice.

The composition may further include at least one metal nanocomposite.

The at least one laser pulse may include an ultrashort laser pulse.

The composition may further include at least one nanocomposite having the additive, and the at least one laser pulse may cause a disruption change to the at least one nanocomposite.

The composition may still further include at least one nanodevice having the additive and a linked therapeutic agent, and the at least one laser pulse may cause the at least one nanodevice to release the linked therapeutic agent.

The composition may still further include at least one nanodevice having the additive, and the at least one laser pulse may cause a disruption change to the at least one nanodevice with little or no damage to material adjacent to the nanodevice.

The at least one laser pulse may cause a disruption change to the at least one nanocomposite with little or no change to material adjacent to the at least one nanocomposite.

The at least one laser pulse may cause a disruption change to the nanocomposite which, in turn, causes a disruption change to material adjacent to the nanocomposite.

The desired photodisruption threshold may be several or more times less than the photodisruption threshold of the composition without the additive.

The desired photodisruption threshold may be one or more orders of magnitude less than the photodisruption threshold of the composition without the additive.

The composition without the additive may include a substantially pure dendrimer and the composition with the additive may include at least one nanocomposite.

The composition may include a plurality of individual nanodevices, and the at least one laser pulse may aggregate the individual nanodevices.

The composition may further include a plurality of nanodevices. Each of the nanodevices may be a nanocomposite having the additive.

Each nanocomposite may be a dendrimer nanocomposite.

Each of the dendrimer nanocomposites may be a metal/dendrimer nanocomposite.

The at least one pulse may cause a change to material in a vicinity of the composition, or may cause material in the vicinity of the composition to be heated, or may cause material in the vicinity of the composition to be broken down.

The composition may include at least one optical data storage nanodevice.

The at least one optical data storage nanodevice may include a dendrimer-based nanodevice.

The at least one nanodevice may include a dendrimer-based nanodevice.

Further in carrying out the above object and other objects of the present invention, a system is provided for enhancing optical breakdown utilizing a composition having an additive incorporated therein. The composition has a desired photodisruption threshold substantially lower than a photodisruption threshold of the composition without the additive. The system includes a pulsed laser for generating at least one laser pulse having a predetermined pulse characteristic based on the desired photodisruption threshold. An optical subsystem directs the at least one laser pulse to the composition. The at least one laser pulse propagates through the composition to a photodisruption region determined by the location of the additive in the composition. The additive decreases the photodisruption threshold associated with the at least one laser pulse in the vicinity of the additive.

The above object and other objects, features, and advantages of the present invention are readily apparent from the following detailed description of the best mode for carrying out the invention when taken in connection with the accompanying drawings.

BRIEF DESCRIPTION OF THE DRAWINGS

FIG. 1a is a schematic view illustrating the architecture of a dendrimer;

FIG. 1b is a schematic view illustrating the architecture of a dendrimer nanocomposite (DNC) used in the method and system of the present invention;

FIG. 1c shows the laser spectrum and the absorption spectra of pure PAMAM and DNC methanol solutions.

DETAILED DESCRIPTION OF THE PREFERRED EMBODIMENTS

Figure 2A:
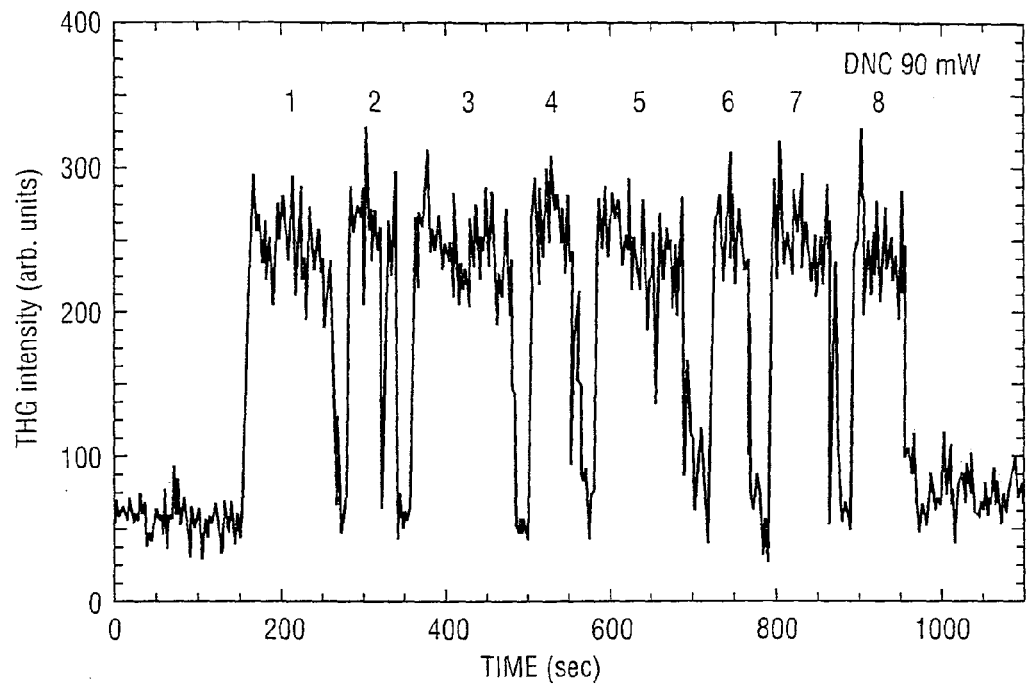
FIG. 2a is a graph which illustrates the change of THG signal during LIOB of DNCs for eight events under laser irradiation of 9 mWs.

In general, the present invention involves an improved laser-based method and system for enhancing optical breakdown using an additive such as metal nanoparticles or metal nanodomains which remarkably change the laser-induced optical breakdown (LIOB) threshold of a material, owing to a large enhancement of the local electric field. In one embodiment, LIOB is implemented using femtosecond laser pulses in a gold/dendrimer hybrid nanocomposite (DNC). Third-harmonic generation measurements have been employed as a sensitive way for monitoring the LIOB in situ and in real-time. The observed statistical behavior of the breakdown process is attributed to a laser-driven aggregation of individual DNC particles. The breakdown threshold value of the DNC has been found to be up to two orders of magnitude lower than that of pure dendrimers or normal tissues.

Dendrimer-based nanoparticles conjugated to linker molecules can be used to selectively deliver the nanoparticles to targeted components in biological systems, and the use of metal nanoparticles or metallic nanocomposites can significantly reduce laser-induced breakdown thresholds, which enhances the effect of triggering release of therapeutics from a drug delivery system with femtosecond laser pulses.

A model system, a gold/dendrimer nanocomposite (DNC), is described using femtosecond laser pulses. A generation-5 poly(amidoamine) (PAMAM) with ethylenediamine (EDA) core was used as a template to form a hybrid nanocomposite. A $4.0 \times 10^{-4}$ M methanol solution of $\{Au(0)_{14}\text{-}PAMAM\_E5.NH_2\}$, which denotes a DNC composed of 14 zero-valent gold atoms per an ethylenediamine core generation-5 PAMAM dendrimer, was held in a quartz cuvette with 1 nun light path and 1 mm thick wall. The laser system used was based on a 250 kHz regeneratively amplified Ti:sapphire laser. The amplified pulses, with pulse duration of 100 fs and wavelength of 793 nm, were attenuated with a variable neutral density filter, and focused at the front interface between the quartz cuvette and the DNC solution using an f:1 off-axis (60°) parabola. Third-harmonic generation (THG) was utilized as a sensitive method for monitoring LIOB in the sample. The THG from the interface was spatially separated from the fundamental transmitted light using a Brewster quartz prism and further filtered with two UV interference band pass filters with center wavelength of 265 nm. The THG signal was monitored during the LIOB process with a photon counting system.

FIGS. 1a and 1b show the architecture of dendrimer and DNC, respectively, and FIG. 1c shows the laser spectrum and the absorption spectra of pure PAMAM and DNC methanol solutions. In contrast to the pure PAMAM dendrimer, the DNC has an absorption maximum around 272 nm, which results from the plasmon resonance of the incorporated gold nanodomains. This absorption peak is close to the one-third of the laser wavelength, while there is no absorption in the wavelength regime of fundamental light.

When the laser power was raised above a certain level, a sudden drop of the THG signal was observed. The variation of THG signal sensitively reflects the change of the material properties, because the intensity of THG is related to the difference of the refractive index or third-order nonlinear susceptibility of the materials on both sides of a laser focus spot at an interface. THG was previously employed to probe the microscopic structure of transparent samples. The THG measurement was used to monitor the LIOB in the DNC sample. In contrast to conventional criteria for determining breakdown threshold by visual acquisition and ablation depth measurement, which is not well defined for the former and not in real-time for the latter, the THG measurements provided a sensitive way to monitor the LIOB in situ and in real-time. In addition, because THG is generated only from an interface, this study was focused on the DNCs adsorbed on or in the vicinity of a surface, since it is known that gold/PAMAM nanocomposites bind to a quartz surface effectively. This system may also serve as a model for DNCs bound to a cell.

Figure 2B:
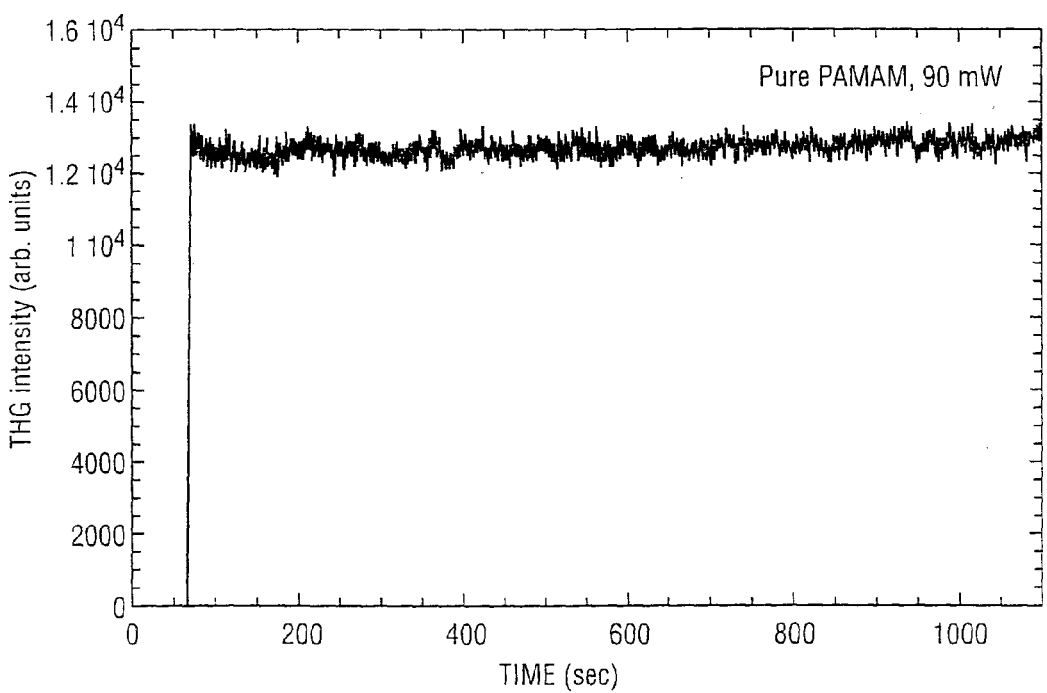
FIG. 2b is a graph which illustrates the THG signal from the pure PAMAM-quartz under irradiation of 90 mW; there is no LIOB observed.

As an example, FIG. 2a shows eight events of breakdown of the DNC sample under irradiation power of 9 mW, where after each breakdown event, the sample was shifted to a new position. The rise of the THG signal occurs when a shutter in the laser beam is opened, while the sudden drop of THG indicates the breakdown. In contrast, FIG. 2b shows that the THG signal from the interface of the quartz and the pure template PAMAM dendrimer remains unchanged even under much higher irradiation power. A breakdown threshold of the DNC was obtained as low as 0.9 mW (9.5 mJ/cm$^2$), while the breakdown threshold of a pure PAMAM dendrimer (without gold) was found to be 102 mW (1080 mJ/cm$^2$), which is 113-fold higher than that of the DNC sample. The breakdown threshold of the DNC is also two orders of magnitude lower than the typical breakdown threshold of a tissue. When irradiating the samples with CW light instead of 100-fs short laser pulses, no breakdown in either DNC or pure PAMAM samples was observed, although the CW laser power was above 420 mW. This finding indicates that the observed breakdown of the samples under the ultrashort-pulse irradiation was due to the high peak laser power. This explanation is also consistent with the fact that there is no linear absorption at the laser wavelength (as shown in FIG. 1c), and thus the possibility for laser-induced thermal breakdown of the sample can be ruled out.

The remarkable reduction of breakdown threshold of DNC compared with that of pure PAMAM dendrimer may be attributed to the enhancement of the local electric field by the gold nanodomains in the nanocomposite. As revealed in recent studies, metal nanoparticles exhibit strong optical extinction owing to resonantly driven electron plasma oscillations (particle plasmons), which leads to an enhancement of the local light field confined on and close to the surface of the metal nanoparticle. Experimental results illustrate that the highly enhanced local field lowers the requirement for the incident laser power by a factor of more than 100 times to cause a disruptive change to the dendrimer structure.

Figure 3:
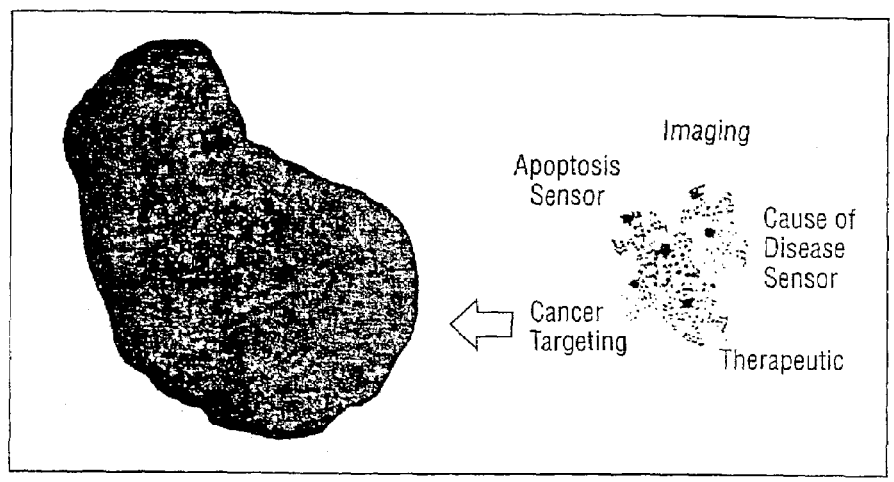
FIG. 3 is a schematic view illustrating the targeting of cancer cells using a dendrimer-based, smart therapeutic nanodevice.

Use of Dendrimer-Based Nanoparticles Conjugated to Linker Molecules to Selectively Deliver the Nanoparticles to Targeted Components in Biological Systems Suitable for Laser Activation When dendrimers are used as a host for metal nanodomains as described herein, one can achieve selectively targeting biological systems, such as a tumor, by modifying the dendrimer peripheral branches with a target agent, as shown in FIG. 3. The large number of peripheral branches of a dendrimer allows one to attach various functional groups to a single dendrimer or to a tecto-dendrimer containing a core dendrimer surrounded by other functional dendrimers. This is one of the remarkable advantages of using dendrimer nanoparticle composites over a pure metal nanoparticle.

There are two possible types of targets to direct the dendrimer-based nanodevice. The first involves the use of cell receptors that are present in normal cells, but over-expressed in cancer cells. These targets would include the receptors for growth factors and would be useful in that they would increase the uptake of the nanodevice specifically in cancer cells and internalize the device through receptor-mediated pinocytosis. An alternative approach would be to target through tumor-specific antigens. This involves targeting cancer-specific proteins such as Her2. In either case, antibodies or specific ligands for the various receptors coupled to dendrimers will be used for targeting.

The specific targeting capability of a conjugated dendrimer has been demonstrated in an uptake experiment of a targeted drug delivery agent into cancer cells. The dendrimers used are conjugated both to a fluorescent dye to enable optical sensing of the presence of dendrimers in the cells, and to folic acid (FA), which enables the dendrimers to be selectively taken up by FA-receptor-positive KB cells (a sub-line derived from the cervical carcinoma HeLa cell line). Specifically, the binding of G5-FI-FA [generation-5 poly (amidoamine) (PAMAM) dendrimers (G5) conjugated with fluorescein isothiocyanate (FI) and FA has been investigated as well as control G5-FI dendrimer to KB cells.

Figure 4A:
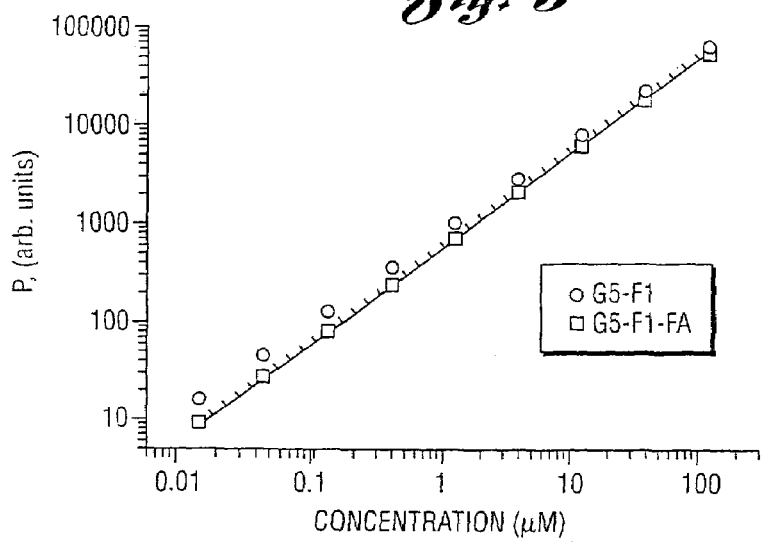
FIG. 4a is a graph which illustrates TPF power as functions of the concentrations of G5-FI and G5-FI-FA.
Figure 4B:
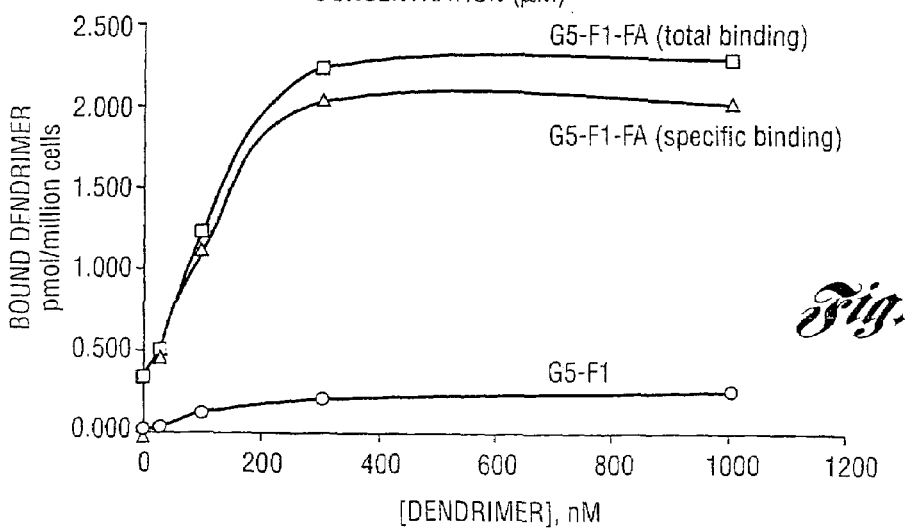
FIG. 4b is a graph of a dose-response curve for the binding of G5-FI and G5-FI-FA on KB cells; the G5-FI-FA specific binding is obtained by subtracting the non-specific G5-FI signal; at saturation, the level of G5-FI-FA bound was about 2 pmol/$10^6$ cells.

First, two-photon fluorescence (TPF) of standard solutions of G5-FI and G5-FI-FA in the absence of KB cells was measured using an optical fiber-based detection system, and exhibited the expected linear concentration dependence, as shown in FIG. 4a. The TPF power from cultured KB cell pellets treated with different concentrations of dendrimer solution was measured. The measured fluorescence can be used to determine quantitatively the number of dendrimer molecules bound to the KB cells. FIG. 4b shows the binding as a function of the concentration used to treat the cells. The total G5-FI-FA bound to the KB cells is significantly higher than that for G5-FI, which is expected since the G5-FI is taken into the cells non-specifically.

Use of Enhanced Laser-Induced Breakdown Using the Above Method for the Triggered Release of Drugs After dendrimer carry therapeutics into cancer cells, one major issue is how to make the therapeutics released from dendrimers to kill cancer cells. One possible way is to use ultrafast laser pulses to break down dendrimer and trigger release of encapsulated drugs. However, the optical breakdown threshold of a dendrimer is almost the same as that of a normal tissue. When triggering the release of therapeutics from a dendrimer, it is necessary to find an appropriate way to avoid lateral damage to excess surrounding tissues by strong laser power. The optical breakdown threshold of a dendrimer can be reduced by a factor of up to 113 times by incorporating gold nanodomains into the dendrimer. This reduction is due to significant enhancement of electrical field localized only to the immediate surrounding of the metal nanodomains. This discovery opens up the possibility to selectively break down dendrimers and activate drugs without optical damage of excess surrounding tissues using a laser fluence lower than the tissue breakdown threshold but higher than that of the dendrimer nanoparticle composites.

The plasmon resonance of the DNC used is in the UV region, far away from the laser wavelength. This suggests that aggregation of the DNCs may be necessary in order to form a cluster with a plasmon resonance near the laser frequency. In an experiment, it was found that there was a waiting time for the breakdown of DNCs and the waiting time fluctuated in a wide range even under the same irradiation conditions. The existence of the waiting time before breakdown implies that it takes some time for individual DNCs to form aggregates and for the aggregates to grow to a critical size. The aggregation leads to a shift of the plasmon resonance in a local region toward the laser wavelength, thus the field of light is enhanced and eventually to exceed the breakdown threshold. The fluctuation of the waiting time reflects the statistical behavior of the aggregation process. Moreover, it has been observed that the waiting time becomes notably shorter when the irradiation power is higher than 40 mW, which is still at a power level lower than the breakdown threshold of a pure dendrimer by a factor of 2.5. The sudden decrease of the waiting time implies that there is a change of the breakdown mechanism for the power above 40 mW.

The unique nature of DNC opens up a wide range of potential applications. The extremely low breakdown threshold would allow one to selectively break down and target DNC molecules to trigger release of encapsulated therapeutics, while avoiding unwanted damage to surrounding tissues. The other potential application is to use DNC to directly break down an organism within a cell (such as a cancer cell) through a nanoheating effect, because the highly enhanced local field of light due to the incorporated metal nanoparticles when irradiated with femtosecond laser pulses is well confined within nanometer region around the DNC. Besides applications in biology and medicine, DNCs may also be used as high-density optical data storage materials owing to their nanometer size and high photosensitivity.

As demonstrated above, the modification of an organic material by incorporating metal nanoparticles to form hybrid nanocomposites significantly reduces the LIOB threshold. A THG measurement was employed to directly monitor the LIOB process. Several applications are possible by taking advantages of the unique nature of the hybrid nanocomposite particles for biology, medicine, and optical data storage.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A laser-based method for enhancing optical breakdown, the method comprising:
    providing a composition having an additive incorporated therein, the composition having a desired photodisruption threshold substantially lower than a photodisruption threshold of the composition without the additive;
    generating at least one laser pulse having a predetermined pulse characteristic based on the desired photodisruption threshold; and
    propagating the at least one laser pulse through the composition to a photodisruption region determined by the location of the additive in the composition wherein the additive decreases the photodisruption threshold associated with the at least one laser pulse in the vicinity of the additive.

2. The method as claimed in claim 1, wherein the composition includes at least one nanodevice having the additive and a linked agent targeted to a specific biological structure or tissue.

3. The method as claimed in claim 2, wherein the at least one nanodevice includes a dendrimer-based nanodevice.

4. The method as claimed in claim 1, wherein the additive includes metal nano particles or domains.

5. The method as claimed in claim 1, wherein the composition includes polymer macromolecules which are a host for the additive.

6. The method as claimed in claim 5, wherein the polymer macromolecules form at least one dendrimer-based nanodevice.

7. The method as claimed in claim 1, wherein the composition includes at least one metal nanocomposite.

8. The method as claimed in claim 1, wherein the at least one laser pulse includes an ultrashort laser pulse.

9. The method as claimed in claim 1, wherein the composition includes at least one nanocomposite having the additive and wherein the at least one laser pulse causes a disruption change to the at least one nanocomposite.

10. The method as claimed in claim 1, wherein the composition includes at least one nanodevice having the additive and a linked therapeutic agent and wherein the at least one laser pulse causes the at least one nanodevice to release the linked therapeutic agent.

11. The method as claimed in claim 1, wherein the composition includes at least one nanodevice having the additive and wherein the at least one laser pulse causes a disruption change to the at least one nanodevice with little or no damage to material adjacent to the nanodevice.

12. The method as claimed in claim 9, wherein the at least one laser pulse causes a disruption change to the at least one nanocomposite with little or no change to material adjacent to the at least one nanocomposite.

13. The method as claimed in claim 9, wherein the at least one laser pulse causes a disruption change to the nanocomposite which, in turn, causes a disruption change to material adjacent to the nanocomposite.

14. The method as claimed in claim 1, wherein the desired photodisruption threshold is several or more times less than the photodisruption threshold of the composition without the additive.

15. The method as claimed in claim 1, wherein the desired photodisruption threshold is one or more orders of magnitude less than the photodisruption threshold of the composition without the additive.

16. The method as claimed in claim 1 wherein the composition without the additive includes a substantially pure dendrimer and the composition with the additive includes at least one nanocomposite.

17. The method as claimed in claim 1, wherein the composition includes a plurality of individual nanodevices and wherein the at least one laser pulse aggregates the individual nanodevices.

18. The method as claimed in claim 1, wherein the composition includes a plurality of nanodevices and wherein each of the nanodevices is a nanocomposite having the additive.

19. The method as claimed in claim 18, wherein each nanocomposite is a dendrimer nanocomposite.

20. The method as claimed in claim 19, wherein each of the dendrimer nanocomposites is a metal/dendrimer nanocomposite.

21. The method as claimed in claim 1, wherein the at least one pulse causes a change to material in a vicinity of the composition.

22. The method as claimed in claim 21, wherein the at least one pulse causes material in the vicinity of the composition to be heated.

23. The method as claimed in claim 21, wherein the at least one pulse causes material in the vicinity of the composition to be broken down.

24. The method as claimed in claim 1, wherein the composition includes at least one optical data storage nanodevice.

25. The method as claimed in claim 24, wherein the at least one optical data storage nanodevice includes a dendrimer-based nanodevice.

26. The method as claimed in claim 10, wherein the at least one nanodevice includes a dendrimer-based nanodevice.

27. A system for enhancing optical breakdown utilizing a composition having an additive incorporated therein, the composition having a desired photodisruption threshold substantially lower than a photodisruption threshold of the composition without the additive, the system comprising:
    a pulsed laser for generating at least one laser pulse having a predetermined pulse characteristic based on the desired photodisruption threshold; and
    an optical subsystem for directing the at least one laser pulse to the composition wherein the at least one laser pulse propagates through the composition to a photodisruption region determined by the location of the additive in the composition wherein the additive decreases the photodisruption threshold associated with the at least one laser pulse in the vicinity of the additive.

28. The system as claimed in claim 27, wherein the composition includes at least one nanodevice having the additive and a linked agent targeted to a specific biological structure or tissue.

29. The system as claimed in claim 28, wherein the at least one nanodevice includes a dendrimer-based nanodevice.

30. The system as claimed in claim 27, wherein the additive includes metal nano particles or domains.

31. The system as claimed in claim 27, wherein the composition includes polymer macromolecules which are a host for the additive.

32. The system as claimed in claim 31, wherein the polymer macromolecules form at least one dendrimer-based nanodevice.

33. The system as claimed in claim 27, wherein the composition includes at least one metal nanocomposite.

34. The system as claimed in claim 27, wherein the at least one laser pulse includes an ultrashort laser pulse.

35. The system as claimed in claim 27, wherein the composition includes at least one nanocomposite having the additive and wherein the at least one laser pulse causes a disruption change to the at least one nanocomposite.

36. The system as claimed in claim 27, wherein the composition includes at least one nanodevice having the additive and a linked therapeutic agent and wherein the at least one laser pulse causes the at least one nanodevice to release the linked therapeutic agent.

37. The system as claimed in claim 27, wherein the composition includes at least one nanodevice having the additive and wherein the at least one laser pulse causes a disruption change to the at least one nanodevice with little or no damage to material adjacent the nanodevice.

38. The system as claimed in claim 35, wherein the at least one laser pulse causes a disruption change to the at least one nanocomposite with little or no change to material adjacent the at least one nanocomposite.

39. The system as claimed in claim 35, wherein the at least one laser pulse causes a disruption change to the nanocomposite which, in turn, causes a disruption change to material adjacent the nanocomposite.

40. The system as claimed in claim 27, wherein the desired photodisruption threshold is several or more times less than the photodisruption threshold of the composition without the additive.

41. The system as claimed in claim 27, wherein the desired photodisruption threshold is one or more orders of magnitude less than the photodisruption threshold of the composition without the additive.

42. The system as claimed in claim 27 wherein the composition without the additive includes a substantially pure dendrimer and the composition with the additive includes at least one nanocomposite.

43. The system as claimed in claim 27, wherein the composition includes a plurality of individual nanodevices and wherein the at least one laser pulse aggregates the individual nanodevices.

44. The system as claimed in claim 27, wherein the composition includes a plurality of nanodevices and wherein each of the nanodevices is a nanocomposite having the additive.

45. The system as claimed in claim 44, wherein each nanocomposite is a dendrimer nanocomposite.

46. The system as claimed in claim 45, wherein each of the dendrimer nanocomposites is a metal/dendrimer nanocomposite.

47. The system as claimed in claim 27, wherein the at least one pulse causes a change to material in a vicinity of the composition.

48. The system as claimed in claim 47, wherein the at least one pulse causes material in the vicinity of the composition to be heated.

49. The system as claimed in claim 47, wherein the at least one pulse causes material in the vicinity of the composition to be broken down.

50. The system as claimed in claim 27, wherein the composition includes at least one optical data storage nanodevice.

51. The system as claimed in claim 50, wherein the at least one optical data storage nanodevice includes a dendrimer-based nanodevice.

52. The system as claimed in claim 36, wherein the at least one nanodevice includes a dendrimer-based nanodevice.

* * * * *